(12) United States Patent
Nishino et al.

(10) Patent No.: US 8,461,550 B2
(45) Date of Patent: Jun. 11, 2013

(54) ELECTRON BEAM STERILIZER

(75) Inventors: Yukinobu Nishino, Kanazawa (JP); Tokuo Nishi, Kanazawa (JP); Yukihiro Yamamoto, Kanazawa (JP)

(73) Assignee: Shibuya Kogyo Co., Ltd., Kanazawa-shi, Ishikawa (JP)

( * ) Notice: Subject to any disclaimer, the term of this patent is extended or adjusted under 35 U.S.C. 154(b) by 0 days.

(21) Appl. No.: 13/308,619

(22) Filed: Dec. 1, 2011

(65) Prior Publication Data

US 2012/0145929 A1 Jun. 14, 2012

(30) Foreign Application Priority Data

Dec. 10, 2010 (JP) ................................. 2010-275738

(51) Int. Cl.
- *G21K 5/10* (2006.01)
- *B65B 55/08* (2006.01)
- *A61L 2/08* (2006.01)

(52) U.S. Cl.
USPC ................ 250/455.11; 250/492.3; 250/491.1; 250/492.1; 422/22

(58) Field of Classification Search
USPC ........ 250/492.3, 492.1, 491.1, 455.11; 422/22
See application file for complete search history.

(56) References Cited

U.S. PATENT DOCUMENTS

| | | |
|---|---|---|
| 6,610,376 B1 | 8/2003 | Rangwalla et al. |
| 2009/0110613 A1* | 4/2009 | Naka et al. ................... 422/186 |
| 2010/0054987 A1* | 3/2010 | Krueger et al. ................... 422/3 |
| 2010/0072395 A1* | 3/2010 | Nishino et al. ........... 250/455.11 |
| 2010/0140507 A1* | 6/2010 | Nishino et al. ............. 250/491.1 |
| 2011/0101248 A1* | 5/2011 | Nishino et al. ............. 250/492.3 |

FOREIGN PATENT DOCUMENTS

| | | |
|---|---|---|
| EP | 1 956 608 A1 | 8/2008 |
| EP | 2 103 528 A1 | 9/2009 |
| EP | 2 141 073 A1 | 1/2010 |
| JP | 09-015399 | 1/1997 |
| JP | 11-038196 | 2/1999 |
| JP | 11-248893 | 9/1999 |
| JP | 2002-082173 | 3/2002 |
| JP | 2003-156598 | 5/2003 |
| JP | 2008-188292 | 8/2008 |

OTHER PUBLICATIONS

European Patent Office Search Report dated Feb. 17, 2012 (9 pages).

* cited by examiner

*Primary Examiner* — Nikita Wells
(74) *Attorney, Agent, or Firm* — Flynn, Thiel, Boutell & Tanis, P.C.

(57) ABSTRACT

Plastic containers fed by an article feeder housed in a shield chamber are sterilized by being irradiated with an electron beam that is radiated from an irradiation window of an electron beam irradiation unit which is coupled to an opening of the shield chamber. In a maintenance mode, an adjustment irradiation box is detachably mounted on the electron beam irradiation unit in covering relation to the irradiation window of the electron beam irradiation unit. The adjustment irradiation box houses therein an electron beam receiver for receiving the electron beam radiated from the irradiation window, a cooling mechanism for cooling the electron beam receiver, and an exhaust mechanism for discharging an atmosphere in the adjustment irradiation box.

5 Claims, 5 Drawing Sheets

FIG. 5B

ELECTRON BEAM STERILIZER

BACKGROUND OF THE INVENTION

1. Field of the Invention

The present invention relates to an electron beam sterilizer for irradiating an article that is being fed by a feeder with an electron beam to sterilize the article, and more particularly to an arrangement for carrying out maintenance work on an electron beam irradiation unit for radiating an electron beam.

2. Description of the Related Art

Electron beam sterilizers generally include an article feeder for successively feeding articles into an isolated sterilization chamber and an electron beam irradiation unit having an irradiation window positioned in facing relation to an opening in the sterilization chamber, thereby coupling the sterilization chamber and the electron beam irradiation unit to each other. Articles that are fed into sterilization chamber by the article feeder are sterilized by an electron beam that is applied from the electron beam irradiation unit through the irradiation window to the articles.

The irradiation window of the electron beam irradiation unit is fitted with a metal foil of titanium or the like. Periodic maintenance work needs to be performed on the irradiation window for replacing the metal foil with a new metal foil, etc. The maintenance work involves not only replacing the metal foil with a new metal foil but also evacuating a chamber of the electron beam irradiation unit after the metal foil has been replaced and actually applying the electron beam to the new metal foil for adjustments.

When the electron beam is applied to the new metal foil for adjustments, the irradiation window of the electron beam irradiation unit is positioned in facing relation to the opening in the sterilization chamber in order to prevent X-rays from leaking out. If the electron beam is applied while the article feeder is not in operation, then the electron beam remains continuously applied to a localized area of the article feeder, tending to overheat and thermally deform the localized area. To avoid such a difficulty, the electron beam is applied while the article feeder is in operation. The process of applying the electron beam to the new metal foil for adjustments after it has replaced the old metal foil usually takes six to seven hours. Therefore, other tasks such as maintenance work on the article feeder cannot be performed during the process, making the electron beam sterilizer inefficient in its operation.

There has already been proposed a technology for preventing articles from being lowered in quality by the application of an electron beam during a maintenance process (see, for example, Japanese laid-open patent publication No. 9-15399). According to the invention disclosed in the above publication, a removable electron beam shield is disposed between an irradiation window and an article which is irradiated with an electron beam to prevent the electron beam from directly reaching the article during the maintenance process. The publication also discloses that the electron beam shield includes a cooling mechanism for dissipating the heat generated when the electron beam shield is irradiated with the electron beam.

According to the invention disclosed in the publication, the electron beam shield is positioned in the processing zone of a feed path along which the article travels. Consequently, the electron beam shield needs to be removed after the maintenance work. However, since ozone that is produced by the applied electron beam leaks out when the electron beam shield is removed, the working environment tends to be adversely affected by the ozone leakage. In addition, it is not easy to install the electron beam shield in the processing zone of the feed path and remove the electron beam shield from the processing zone of the feed path. Furthermore, it is not possible to carry out maintenance work on the article feeder while maintenance work is being performed on the electron beam irradiation unit.

OBJECTS AND SUMMARY OF THE INVENTION

It is an object of the present invention to provide an electron beam sterilizer which prevents an article feeder from being adversely affected, i.e., over-heated, by the application of an electron beam when an electron beam irradiation unit is adjusted after its maintenance work is over.

Another object of the present invention is to provide an electron beam sterilizer which is made efficient operation by allowing maintenance work to be performed on an article feeder while maintenance work is being carried out on an electron beam irradiation unit.

Still another object of the present invention is to provide an electron beam sterilizer which prevents the atmosphere in an adjustment box irradiated with an electron beam from leaking out of the adjustment box.

To achieve the above objects, there is provided in accordance with the present invention an electron beam sterilizer for sterilizing an article by applying an electron beam thereto, comprising an electron beam irradiation unit having an irradiation window for applying an electron beam therethrough, an adjustment irradiation box adapted to be removably coupled to the electron beam irradiation unit in covering relation to the irradiation window, an electron beam receiver disposed in the adjustment irradiation box for receiving the electron beam applied from the electron beam irradiation unit, an exhaust mechanism for discharging an atmosphere in the adjustment irradiation box from the adjustment irradiation box, and a cooling mechanism for cooling the electron beam receiver.

According to the present invention, the adjustment irradiation box is coupled to the electron beam irradiation unit in covering relation to the irradiation window, and the electron beam receiver disposed in the adjustment irradiation box receives the electron beam applied from the electron beam irradiation unit. As the adjustment irradiation box is coupled to the electron beam irradiation unit, an article feeder which feeds the article when it is sterilized is not overheated by the electron beam. While maintenance work is being carried out on the electron beam irradiation unit, the article feeder and other components in the shield chamber can be serviced for maintenance. Since the adjustment irradiation box is combined with the exhaust mechanism, the atmosphere in the adjustment irradiation box which is irradiated with the electron beam does not leak out of the adjustment irradiation box.

The electron beam sterilizer further includes article feeding means for feeding the article, and a sterilization chamber housing the article feeding means therein, wherein the sterilization chamber includes an opening defined therein, and the electron beam sterilizer is selectively operable in a sterilization mode in which the irradiation window of the electron beam irradiation unit is disposed in facing relation to the opening of the sterilization chamber and a maintenance mode in which the electron beam irradiation unit is disconnected from the sterilization chamber and connected to the adjustment irradiation box.

The electron beam receiver is of a size having vertical and horizontal dimensions greater than the irradiation window, whereby the electron beam receiver can receive the electron beam from the electron beam irradiation unit in its entirety.

The electron beam sterilizer further includes measuring means for measuring the value of a current flowing in the electron beam receiver when the electron beam receiver is irradiated with the electron beam, comparing means for comparing the measured value of the current with a reference value, and decision means for determining the dose of the applied electron beam is normal or not based the result of the comparison made by the comparing means.

The electron beam receiver includes a plurality of separate dose films, and the electron beam sterilizer further includes means for determining whether an entire area of the irradiation window is normal or not by measuring respective doses of the electron beam on the separate dose films after the electron beam receiver is irradiated with the electron beam.

The above and other objects, features, and advantages of the present invention will become apparent from the following description when taken in conjunction with the accompanying drawings which illustrate a preferred embodiment of the present invention by way of example.

DETAILED DESCRIPTION OF THE PREFERRED EMBODIMENTS

Electron beam sterilizers according to preferred embodiments of the present invention will be described below. According to the preferred embodiments, an article feeder which is disposed in a sterilization chamber serving as a shield chamber feeds articles such as containers or the like that are introduced from outside of the sterilization chamber. The sterilization chamber has an opening defined in a wall thereof. An electron beam irradiation unit has an irradiation window disposed in facing relation to the opening of the sterilization chamber. The electron beam irradiation unit applies an electron beam through the irradiation window to an article fed by the article feeder to sterilize the article. The electron beam irradiation unit is separable from the sterilization chamber. When the electron beam irradiation unit is separate from the sterilization chamber, a titanium film on the irradiation window is replaced with a new titanium film. An adjustment irradiation box is removably mounted on the electron beam irradiation unit in surrounding relation to the irradiation window of the electron beam irradiation unit. The adjustment irradiation box houses therein an electron beam receiver for receiving the electron beam applied from the electron beam irradiation unit through the irradiation window, a cooling mechanism for cooling the electron beam receiver, and an exhaust mechanism for discharging an internal atmosphere out of the adjustment box. For carrying out maintenance work on the electron beam irradiation unit, the adjustment irradiation box is mounted on the electron beam irradiation unit in surrounding relation to the irradiation window thereof. Consequently, during the maintenance work on the electron beam irradiation unit, the article feeder in the sterilization chamber does not need to be actuated, but processes such as a maintenance process can be performed on the article feeder.

The electron beam sterilizers according to the preferred embodiments of the present invention will be described below with reference to the drawings.

Like or corresponding parts are denoted by like or corresponding reference characters throughout views.

First Embodiment

Figure 1:
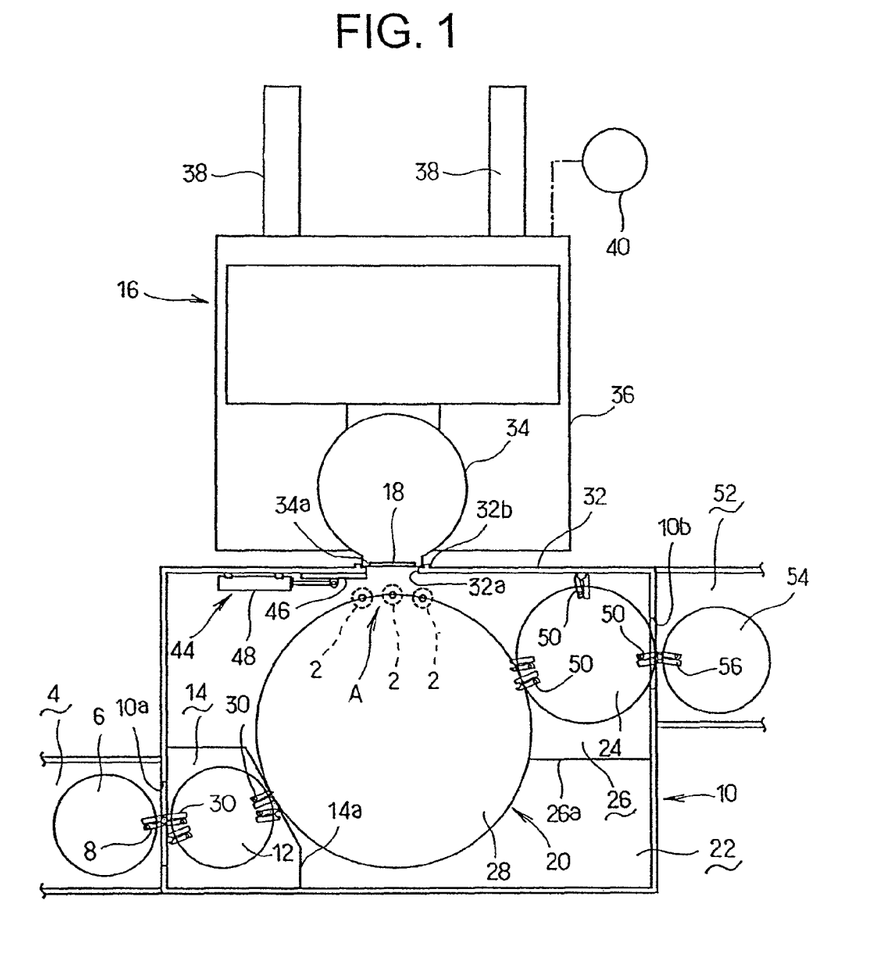
FIG. 1 is a plan view of an electron beam sterilizer according to a first embodiment of the present invention.

FIG. 1 is a plan view of an electron beam sterilizer according to a first embodiment of the present invention. As shown in FIG. 1, a container 2 which is irradiated and sterilized with an electron beam emitted from an electron beam sterilizer and which will subsequently be filled with contents such as a liquid is a plastic container such as a PET bottle or the like. The plastic container 2 has on its neck a flange supported at its lower surface by a support rail of an air feed conveyor, not shown. The plastic container 2 is fed along the air feed conveyor to the electron beam sterilizer by a jet of air applied to the rear side of the plastic container 2. When the plastic container 2 is fed to the electron beam sterilizer, the plastic container 2 is introduced into an introduction chamber 4 wherein the plastic container 2 is transferred to a loading wheel 6 disposed therein.

The loading wheel 6 in the introduction chamber 4 has a plurality of container grippers 8 as container holding means spaced at equal angular intervals around a circumferential edge thereof. While the loading wheel 6 is in rotation about its own axis, the container grippers 8 receive a succession of plastic containers 2 from the air feed conveyor, which is positioned upstream of the loading wheel 6, and feed the received plastic containers 2 down a feed path along the circumferential edge of the loading wheel 6.

The introduction chamber 4 is followed by a shield chamber (sterilization chamber) 10 defined by walls of lead which block an electron beam and X-rays (damping X-rays) against leakage from the shield chamber 10 when each plastic container 2 is irradiated with the electron beam and sterilized thereby. The shield chamber 10 is divided into a supply compartment 14 connected to the introduction chamber 4 and housing a supply wheel 12 therein, a main compartment 22 housing therein a rotary container feeder 20 for feeding a plastic container 2 received from the supply wheel 12 and moving the plastic container 2 in front of an electron beam irradiation window 18 of an electron beam irradiating device 16, to be described later, and a discharge compartment 26 housing therein a discharge wheel 24 for receiving a plastic container 2 which has been irradiated with an electron beam applied from the electron beam irradiating device 16 and sterilized thereby, and discharging the received plastic container 2.

The shield chamber 10 has a wall shared by the introduction chamber 4 and the supply compartment 14. The wall has an opening 10a defined therein through which the plastic container 2 can move from the loading wheel 6 in the introduction chamber 4 to the supply wheel 12 in the supply compartment 14. When the supply wheel 12 has received the plastic container 2 from the loading wheel 6 in the introduction chamber 4, the supply wheel 12 transfers the received plastic container 2 to the rotary container feeder 20 in the main compartment 22. The supply compartment 14 has a partition 14a shared by the supply compartment 14 and the main compartment 22 and having an opening, not shown, defined therein, through which the plastic container 2 can pass from the supply wheel 12 to the rotary container feeder 20 in the main compartment 22.

The rotary container feeder 20 includes a rotor 28 having a plurality of container grippers, not shown, as container support means spaced at equal angular intervals around a circumferential edge thereof. The supply wheel 12 in the supply compartment 14 also has a plurality of container grippers 30 as container holding means spaced at equal angular intervals around a circumferential edge thereof. While the supply wheel 12 is in rotation about its own axis, the container grippers 30 receive a succession of plastic containers 2 from the container grippers 8 on the loading wheel 6, and feed the received plastic containers 2 down a feed path along the circumferential edge of the supply wheel 12. While the rotor 28 is in rotation about its own axis, the container grippers thereof receive a succession of plastic containers 2 from the container grippers 30 on the supply wheel 12, and feed the received plastic containers 2 down a feed path along the circumferential edge of the rotor 28.

The electron beam irradiating device 16 is disposed adjacent to a side wall 32, shown as an upper side wall in FIG. 1, of the shield chamber 10. The electron beam irradiating device 16 includes an electron beam irradiation unit 34 for irradiating a plastic container 2 with an electron beam, and is placed on a table 36. The irradiation window 18 is actually provided on the electron beam irradiation unit 34. The electron beam irradiating device 16, which is of known nature, operates as follows: A filament in a vacuum in the electron beam irradiation unit 34 is heated to generate thermions, which are accelerated under a high voltage into a high-speed electron beam. The electron beam is emitted out of the electron beam irradiation unit 34 into the main chamber 22 through a metal window foil of aluminum (Al) or titanium (Ti) mounted on the irradiation window 18, and applied to objects, i.e., plastic containers 2, placed in the main chamber 22, thereby sterilizing the plastic containers 2.

Figure 2:
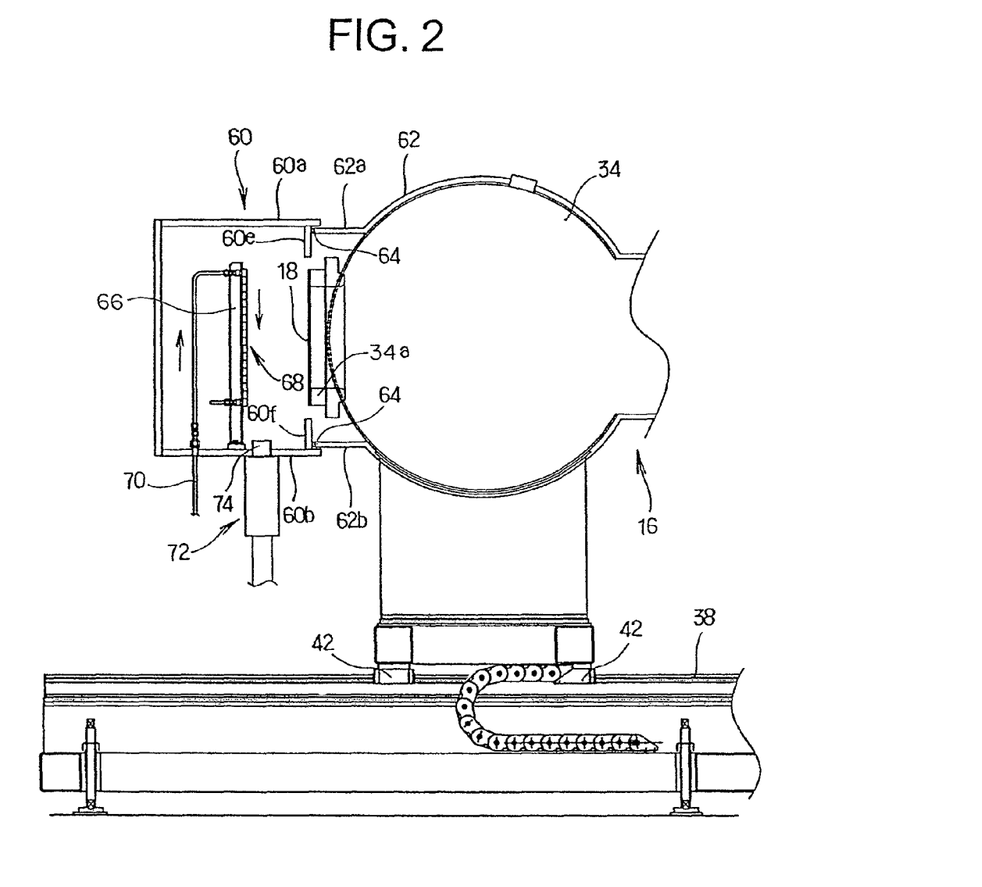
FIG. 2 is a vertical cross-sectional view of an electron beam irradiation unit and an adjustment box, which are coupled to each other, of the electron beam sterilizer according to the first embodiment.

According to the first embodiment, the table 36 with the electron beam irradiating device 16 mounted thereon is movable on two rails 38 and can be moved along the rails 38 toward and away from the shield chamber 10 by a motor 40. The two rails 38 are disposed parallel to each other and extend in directions perpendicular to the side wall 32 of the shield chamber 10. As shown in FIG. 2, a plurality of sliders 42 which are mounted on a lower surface of the table 36 are held in sliding engagement with the rails 38. When the motor 40 is energized, the sliders 42 allow the electron beam irradiation unit 34 to move along the rails 38 toward and away from the shield chamber 10. For operating the electron beam sterilizer, the table 36 is displaced toward the shield chamber 10 until the electron beam irradiation window 18 of the electron beam irradiation unit 34 is aligned with and faces a rectangular opening 32a that is defined in the side wall 32 of the shield chamber 10. The electron beam irradiation unit 34 and the shield chamber 10 are then coupled to each other. An electron beam irradiation zone A is defined in the main chamber 22 in front of the irradiation window 18 on the feed path along the rotary container feeder 20. When the electron beam sterilizer is in operation, the plastic containers 2 that are held in a vertical attitude by the container grippers on the rotor 28 are successively sterilized by the electron beam applied from the electron beam irradiating device 16 through the irradiation window 18 and the rectangular opening 32a while the plastic containers 2 are successively passing through the electron beam irradiation zone A.

The junction between the shield chamber 10 and the electron beam irradiating device 16 will briefly be described below. The rectangular opening 32a that is defined in the side wall 32 is surrounded by a ridge 32b on an outer surface of the side wall 32 which faces the electron beam irradiating device 16. The ridge 32b is slightly spaced outwardly from the rectangular opening 32a, leaving a stepped edge around the rectangular opening 32a. The stepped edge serves as a joint for connection to the electron beam irradiation unit 34.

The irradiation window 18 of the electron beam irradiation unit 34 includes a rectangular window frame 34a projecting from the electron beam irradiation unit 34 toward the shield chamber 10. When the irradiation window 18 is positioned near the opening 32a in alignment therewith, the rectangular window frame 34a fits the stepped edge, i.e., the joint, provided around the rectangular opening 32a by the ridge 32b, and is surrounded by the ridge 32b. A seal member, not shown, is mounted on the surface of the rectangular window frame 34a. When the rectangular window frame 34a is pressed against the joint around the rectangular opening 32a under a certain pressure, therefore, the shield chamber 10 and the electron beam irradiating device 16 are hermetically coupled to each other. The rectangular window frame 34a that is pressed against the joint around the rectangular opening 32a and surrounded by the ridge 32b is effective to prevent X-rays and electron beams from leaking from the junction between the shield chamber 10 and the electron beam irradiating device 16. In FIG. 1, the electron beam irradiation window 18 of the electron beam irradiation unit 34 is shown as joined to the stepped edge around the rectangular opening 32a of the shield chamber 10.

According to the first embodiment, the electron beam sterilizer includes a closure means 44 for closing the rectangular opening 32a of the shield chamber 10. The closure means 44 has a shutter 46 for covering the rectangular opening 32a in the shield chamber 10 and an air cylinder 48 as a shutter opening and closing means for moving the shutter 46 to selectively open and close the rectangular opening 32a. The air cylinder 48 is oriented horizontally and fixed to an inner surface of the side wall 32. The air cylinder 48 includes a piston rod having a distal end coupled to a rear surface of the shutter 46. A seal member, not shown, is mounted on a front surface of the shutter 46 which faces the side wall 32. When the shutter 46 closes the rectangular opening 32a, therefore, the seal member provides a hermetic seal around the rectangular opening 32a.

As described above, the electron beam irradiation zone A is defined in the main chamber 22 in front of the irradiation window 18, so that a plastic container 2 can be irradiated with the electron beam in the electron beam irradiation zone A. The discharge compartment 26 extends from an area where the irradiated plastic container 2 fed by the rotary container feeder 20 leaves the electron beam irradiation zone A, and is defined by a partition 26a in the main compartment 22 and an upper wall, not shown, of the shield chamber 10. The irradiated plastic container 2 which has left the electron beam irradiation zone A is transferred from the corresponding container gripper on the rotor 28 of the rotary container feeder 20 to the discharge wheel 24 that is disposed in the discharge chamber 26. The discharge wheel 24 has a plurality of container grippers 50 as container holding means spaced at equal angular intervals around a circumferential edge thereof. A plastic container 2 which is transferred from one of the container gripper 28 of the rotary container feeder 20 is received and held by one of the container grippers 50 on the discharge wheel 24, and discharged into the discharge compartment 26.

The discharge wheel 24 in the discharge compartment 26 transfers a plastic container 2 received from the rotary container feeder 20 to one of container grippers 56 as container holding means on an unloading wheel 54 in an intermediate chamber 52 which is disposed adjacent to the shield chamber 10. The plastic container 2 is then delivered from the intermediate chamber 52 to downstream processes including a filling process and a capping process. The shield chamber 10 has a wall shared by the intermediate chamber 52 and the discharge compartment 26. The wall has an opening 10b defined therein through which the plastic container 2 can move from the discharge wheel 24 in the discharge compartment 26 to the unloading wheel 54 in the intermediate chamber 52.

Figure 3:
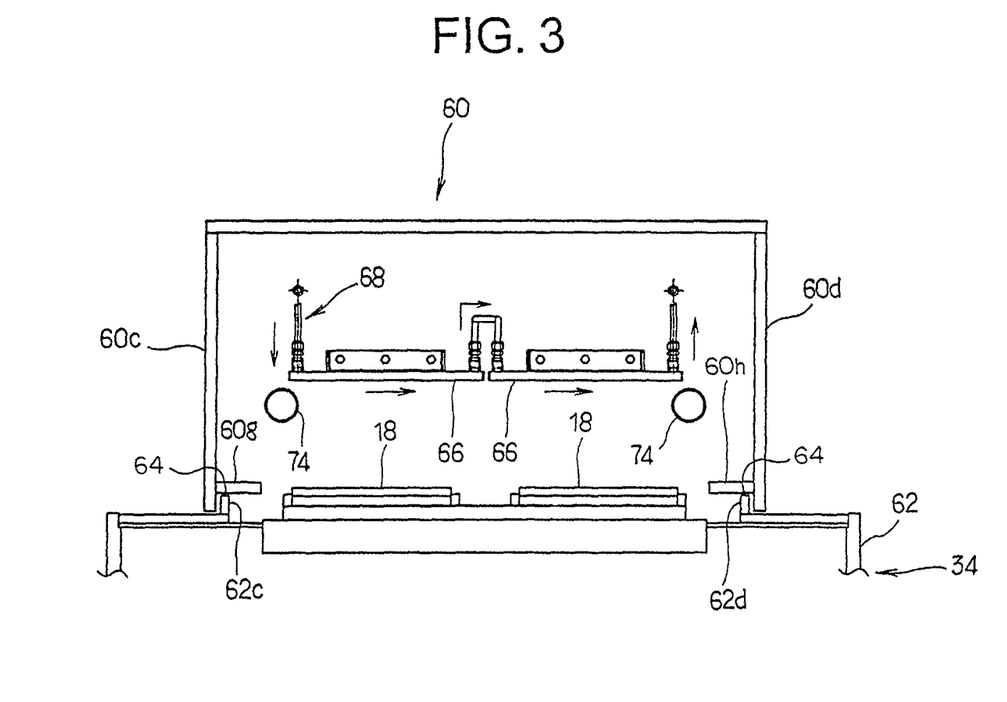
FIG. 3 is a fragmentary horizontal cross-sectional view of the electron beam irradiation unit and the adjustment box which are coupled to each other.

According to the first embodiment, the shield chamber 10 and the electron beam irradiating device 16 are separably coupled to each other. When the electron beam sterilizer is in operation, the shield chamber 10 and the electron beam irradiating device 16 are coupled to each other as shown in FIG. 1. For performing maintenance work on the electron beam irradiating device 16 to replace the metal window foil on the irradiation window 18, the electron beam irradiating device 16 is separated from the shield chamber 10, and an adjustment irradiation box 60 shown in FIGS. 2 and 3 is coupled to the irradiation window 18.

The adjustment irradiation box 60 is in the shape of a rectangular parallelepiped whose vertical and horizontal dimensions are greater than the irradiation window 18. The adjustment irradiation box 60 has a front side which is open toward the irradiation window 18. As shown in FIGS. 2 and 3, the adjustment irradiation box 60 includes an upper wall 60a, a lower wall 60b, a left wall 60c, and a right wall 60d with short joint plates 60e, 60f, 60g, 60h fixed respectively to inner surfaces thereof. As with the shield chamber 10, the adjustment irradiation box 60 has walls, including the walls 60a through 60d, made of lead which block an electron beam and X-rays (damping X-rays) against leakage from the adjustment irradiation box 60. The electron beam irradiating device 16 includes a joint frame 62 disposed around the electron beam irradiation unit 34 for connection to the adjustment irradiation box 60. The joint frame 62 includes an upper tip end wall 62a, a lower tip end wall 62b, a left tip end wall 62c, and a right tip end wall 62d. These tip end walls 62a through 62d jointly provide a rectangular shape that is of a size to be snugly held against the inner surfaces of the walls 60a through 60d of the adjustment irradiation box 60. Seal members 64 are mounted respectively on the distal ends of the tip end walls 62a through 62d. When the joint frame 62 is connected to the adjustment irradiation box 60, the tip end walls 62a through 62d are held against the respective inner surfaces of the walls 60a through 60d of the adjustment irradiation box 60, and the seal members 64 are pressed against the joint plates 60e through 60h of the adjustment irradiation box 60, thereby securing the electron beam irradiation unit 34 and the adjustment irradiation box 60 to each other to provide a hermetic seal in their junction against the leakage of an electron beam therefrom.

The adjustment irradiation box 60 houses therein an electron beam receiver 66 for receiving an electron beam radiated from the electron beam irradiation unit 34. When the electron beam irradiation unit 34 and the adjustment irradiation box 60 are coupled to each other, the electron beam receiver 66 is positioned in front of the irradiation window 18 and lies parallel to the irradiation window 18. The electron beam receiver 66 is of a size having vertical and horizontal dimensions greater than the irradiation window 18 for receiving the electron beam in its entirety. According to the first embodiment, the irradiation window 18 is divided into two window sections that are horizontally spaced from each other, and the electron beam receiver 66 has a width covering these two window sections of the irradiation window 18, as shown in FIG. 3. The electron beam receiver 66 is combined with a cooling mechanism 68 for cooling the front surface thereof which is bombarded with the electron beam radiated from the electron beam irradiation unit 34. The cooling mechanism 68 allows a coolant supplied from an external conduit 70 to flow therethrough in the directions indicated by the arrows in FIGS. 2 and 3 for thereby cooling the front surface of the electron beam receiver 66 which has been heated by the electron beam applied thereto.

As shown in FIG. 2, the adjustment irradiation box 60 also includes an exhaust mechanism 72 for discharging an internal atmosphere out of the adjustment irradiation box 60. The exhaust mechanism 72 has an exhaust pipe 74 mounted on the lower wall 60b of the adjustment irradiation box 60 and having an end which is open into the adjustment irradiation box 60, and a suction means, not shown, connected to the other end of the exhaust pipe 74.

The electron beam sterilizer according to the first embodiment operates as follows: When the electron beam sterilizer is to sterilize plastic containers 2, the electron beam irradiating device 16 is displaced toward the shield chamber 10 until the joint, around the opening 32a, of the shield chamber 10 and the rectangular window frame 34a of the electron beam irradiation unit 34 are closely held against and coupled to each other as shown in FIG. 1. Although a plurality of plastic containers 2 are successively supplied to the electron beam sterilizer in reality, an operation sequence with respect to only one plastic container 2 will be described below. A plastic container 2 which is fed by the air feed conveyor, not shown, is introduced into the introduction chamber 4 wherein the plastic container 2 is transferred to a container gripper 8 on the loading wheel 6. After being fed by the loading wheel 6, the plastic container 2 is transferred to and held by a container gripper 30 on the supply wheel 12 in the supply compartment 14 in the shield chamber 10. Thereafter, the plastic container 2 is fed by the supply wheel 12 and then transferred to and held by a container gripper, not shown, on the rotor 28 of the rotary container feeder 20 in the main compartment 22.

As the rotor 28 rotates about its own axis, the plastic container 2 which is held by the container gripper on the rotor 28 is fed into the electron beam irradiation zone A in front of the irradiation window 18 of the electron beam irradiation unit 34. Since the electron beam irradiation zone A is constantly irradiated from the electron beam emitted from the irradiation window 18, the plastic container 2 is irradiated and hence sterilized with the electron beam emitted from the irradiation window 18 as it is being fed by the rotary container feeder 20. The sterilized plastic container 2 is then transferred from the container gripper on the rotary container feeder 20 to a container gripper 50 on the discharge wheel 24. The sterilized plastic container 2 is then transferred from the container gripper 50 on the discharge wheel 24 to a container gripper 56 on the unloading wheel 54 in the intermediate chamber 52. Thereafter, the sterilized plastic container 2 is delivered from the intermediate chamber 52 to downstream processes including a filling process and a capping process.

The electron beam irradiation unit 34 needs to periodically replace the metal window foil of aluminum or titanium mounted on the irradiation window 18 in a maintenance process. For performing the maintenance process, the motor 40 is energized to retract the electron beam irradiating device 16 from the shield chamber 10. At this time, the air cylinder 48 of the closure means 44 on the inner surface of the side wall 32 of the shield chamber 10 is actuated to move the shutter 46 over the opening 32a of the shield chamber 10, thereby closing the opening 32a.

Then, the metal window foil on the irradiation window 18 is replaced with a new metal window foil. Thereafter, in order to perform adjustment work on the electron beam irradiation unit 34, the adjustment irradiation box 60 is coupled to the electron beam irradiation unit 34 which has been disconnected from the shield chamber 10. At this time, the seal members 64 on the tip end walls 62a through 62d of the joint frame 62 of the electron beam irradiation unit 34 are pressed against the short joint plates 60e, 60f, 60g, 60h fixed respectively to the inner surfaces of the adjustment irradiation box 60. Thereafter, the electron beam irradiation unit 34 is evacuated, and actually emits an electron beam for adjustments. The electron beam radiated from the electron beam irradiation unit 34 through the irradiation window 18 is received by the electron beam receiver 66 housed in the adjustment irradiation box 60. At this time, the cooling mechanism 68 prevents the electron beam receiver 66 from being overheated by the electron beam. The exhaust mechanism 72 coupled to the adjustment irradiation box 60 discharges ozone produced when the electron beam is radiated. Therefore, no ozone leaks out when the adjustment irradiation box 60 and the electron beam irradiation unit 34 are separated from each other after the adjustment work.

In the present embodiment, the electron beam irradiation unit 34 is disconnected from the shield chamber 10 for performing maintenance work on the electron beam irradiation unit 34. Since the adjustment irradiation box 60 whose walls are made of lead as with the shield chamber 10 is connected to the front side of the irradiation window 18 in a hermetically sealed fashion, no electron beam and no X-rays (damping X-rays) will leak out of the adjustment irradiation box 60. Furthermore, inasmuch as the shield chamber 10 with the rotary container feeder 20 housed therein is separated from the electron beam irradiation unit 34, the rotary container feeder 20 can independently be processed. Specifically, desired tasks such as a maintenance process can be performed on the rotary container feeder 20 at the same time as the maintenance and adjustment work on the electron beam irradiation unit 34. In addition, since the opening 32a of the shield chamber 10 is closed by the closure means 44, the shield chamber 10 can be used to process plastic containers 2 or other articles in a mode of operation which does not use the electron beam irradiation unit 34.

Second Embodiment

Figure 4:
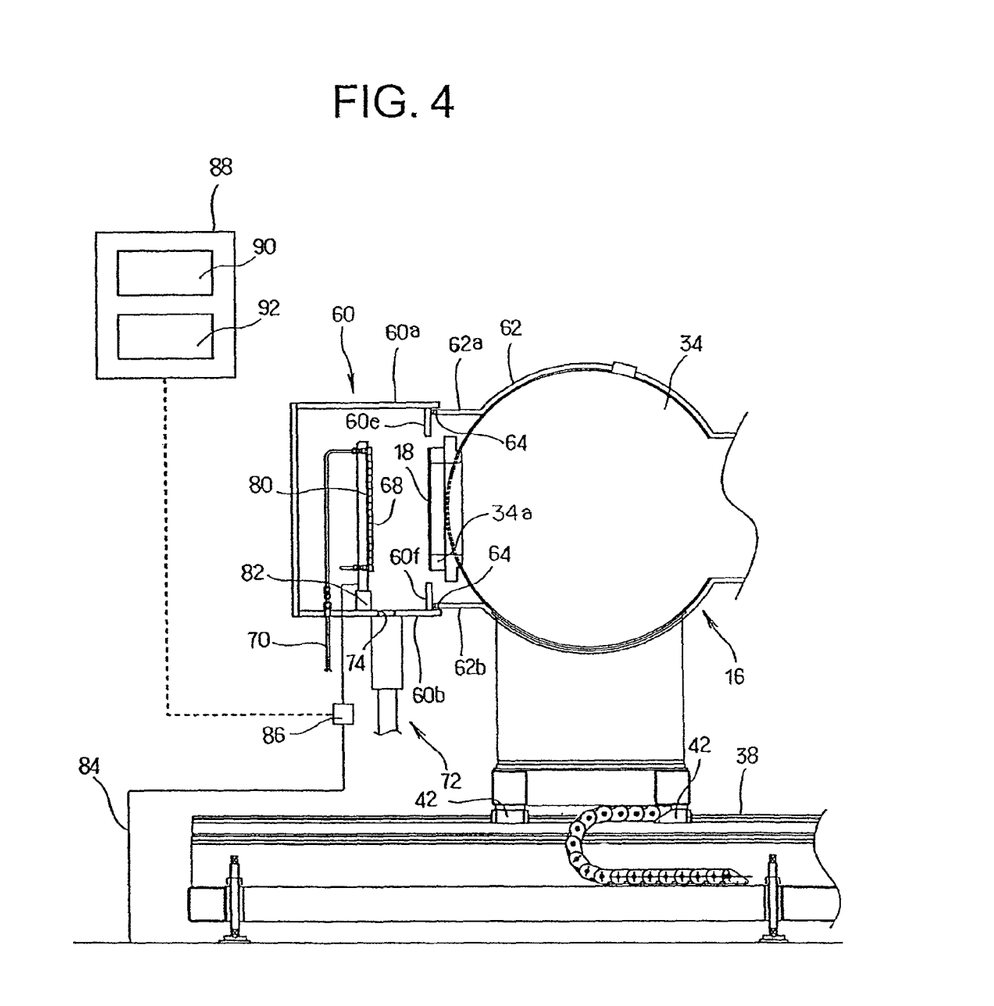
FIG. 4 is a vertical cross-sectional view of an electron beam irradiation unit and an adjustment box, which are coupled to each other, of an electron beam sterilizer according to a second embodiment of the present invention.

An electron beam sterilizer according to a second embodiment of the present invention will be described below with reference to FIG. 4. As shown in FIG. 4, the electron beam sterilizer according to the second embodiment includes an electron beam irradiation unit 34 and an adjustment irradiation box 60 coupled thereto, which are basically identical in structure to those of the electron beam sterilizer according to the first embodiment. The electron beam sterilizer according to the second embodiment resides in that it additionally includes a means for detecting whether the dose of an electron beam radiated from the electron beam irradiation unit 34 is normal or not. Those parts of the electron beam sterilizer according to the second embodiment which are identical to those of the electron beam sterilizer according to the first embodiment are denoted by identical reference characters, and will not be described in detail below, and only features unique to the second embodiment will be described below. According to the second embodiment, the adjustment irradiation box 60 houses therein an electron beam receiver 80 which also doubles as a current measuring electrode for measuring the dose of an applied electron beam. The electron beam receiver 80 is supported by a support 82 made of an insulating material in the adjustment irradiation box 60. The electron beam receiver 80 is connected to ground by a ground line 84 with a current measuring means 86 such as an ammeter connected thereto. The current measuring means 86 measures a current flowing from the electron beam receiver 80 through the ground line 84 to ground when the electron beam receiver 80 is irradiated with an electron beam radiated from the electron beam irradiation unit 34.

The value of the current which is measured by the current measuring means 86 is sent to a controller 88 including a comparator 90 and a decision section 92. The comparator 90 compares the measured value of the current with a reference value stored in the controller 88. The decision section 92 determines whether the dose of the electron beam radiated from the electron beam irradiation unit 34 is normal or not based on the result of the comparison made by the comparator 90. According to the second embodiment, therefore, it is possible to confirm whether the dose of the electron beam radiated from the electron beam irradiation unit 34 is normal or not by measuring the value of a current which flows from the electron beam receiver 80 through the ground line 84 to ground when the electron beam receiver 80 is irradiated with the electron beam.

Third Embodiment

Figure 5A:
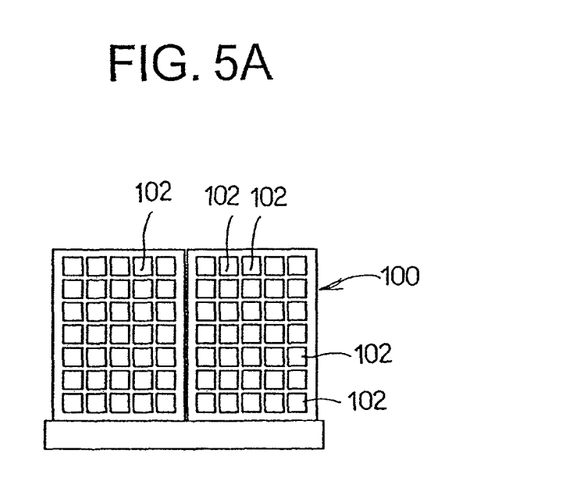
FIG. 5A is a front elevational view of an electron beam receiver to be installed in an adjustment radiation box of an electron beam sterilizer according to a third embodiment of the present invention.
Figure 5B:
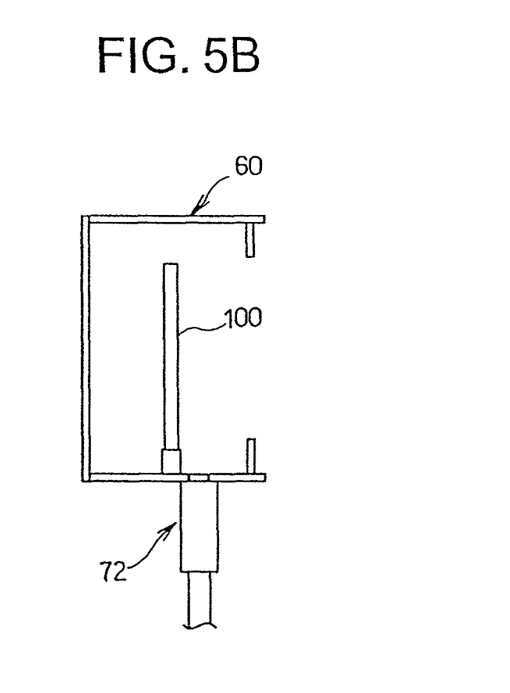
FIG. 5B is a side elevational view of the electron beam receiver installed in the adjustment radiation box shown in FIG. 5A.

FIGS. 5A and 5B show an adjustment radiation box 60 of an electron beam sterilizer according to a third embodiment of the present invention. According to the third embodiment, the adjustment radiation box 60 houses therein an electron beam receiver 100 with a number of small separate dose films 102 mounted on its entire front surface which faces the irradiation window 18. The dose films 102 are manually installed on and removed from the electron beam receiver 100. In operation, the electron beam receiver 100 with the dose films 102 mounted on its entire front surface is placed in the adjustment radiation box 60, and the adjustment radiation box 60 is coupled to the electron beam irradiation unit 34. Then, the electron beam receiver 100 is irradiated with an electron beam radiated from the electron beam irradiation unit 34.

After the electron beam receiver 100 is irradiated with the electron beam, the dose films 102 are removed one by one from the electron beam receiver 100, and the doses of the electron beam applied to the dose films 102 are measured by a dosimeter, not shown, to check if a predetermined dose is indicated by all the dose films 102 or not. If the predetermined dose is indicated by all the dose films 102, then it is decided that the entire area of the irradiation window 18 of the electron beam irradiation unit 34 is normal.

The arrangement according to the third embodiment is used to check if the entire area of the irradiation window 18 of the electron beam irradiation unit 34 is normal or not after it is decided that the dose of the applied electron beam is normal based on the value of the current measured by the arrangement according to the second embodiment. To perform such a two-stage inspection, the adjustment irradiation box 60 with the electron beam receiver 80 shown in FIG. 4 and the adjustment irradiation box 60 with the dose films 102 mounted on the electron beam receiver 100 shown in FIGS. 5A and 5B may be placed in succession. Alternatively, the electron beam receivers 80, 100 may be removably placed selectively in the adjustment irradiation box 60, and after the electron beam receiver 80 shown in FIG. 4 is placed in the adjustment irradiation box 60 to measure the current, the electron beam receiver 80 may be removed and the electron beam receiver 100 shown in FIGS. 5A and 5B may be placed in the same adjustment irradiation box 60 to measure the doses of the electron beam on the dose films 102.

Although certain preferred embodiments of the present invention have been shown and described in detail, it should be understood that various changes and modifications may be made therein without departing from the scope of the appended claims.

What is claimed is:

1. An electron beam sterilizer for sterilizing an article by applying an electron beam thereto, comprising:
   an electron beam irradiation unit having an irradiation window for applying an electron beam therethrough;
   an adjustment irradiation box adapted to be removably coupled to said electron beam irradiation unit in covering relation to said irradiation window;
   an electron beam receiver disposed in said adjustment irradiation box for receiving the electron beam applied from said electron beam irradiation unit;
   an exhaust mechanism for discharging an atmosphere in said adjustment irradiation box from the adjustment irradiation box; and
   a cooling mechanism for cooling said electron beam receiver.

2. An electron beam sterilizer according to claim 1, wherein said electron beam receiver is of a size having vertical and horizontal dimensions greater than said irradiation window, whereby said electron beam receiver can receive the electron beam from said electron beam irradiation unit in its entirety.

3. An electron beam sterilizer according to claim 1, further comprising:
   measuring means for measuring the value of a current flowing in said electron beam receiver when the electron beam receiver is irradiated with the electron beam;
   comparing means for comparing the measured value of the current with a reference value; and
   decision means for determining the dose of the applied electron beam is normal or not based on the result of the comparison made by said comparing means.

4. An electron beam sterilizer according to claim 2, wherein said electron beam receiver includes a plurality of separate dose films, further comprising:
   means for determining whether an entire area of said irradiation window is normal or not by measuring respective doses of the electron beam on said separate dose films after the electron beam receiver is irradiated with the electron beam.

5. An electron beam sterilizer for sterilizing an article by applying an electron beam thereto, comprising:
   an electron beam irradiation unit having an irradiation window for applying an electron beam therethrough;
   an adjustment irradiation box adapted to be removably coupled to said electron beam irradiation unit in covering relation to said irradiation window;
   an electron beam receiver disposed in said adjustment irradiation box for receiving the electron beam applied from said electron beam irradiation unit;
   an exhaust mechanism for discharging an atmosphere in said adjustment irradiation box from the adjustment irradiation box;
   a cooling mechanism for cooling said electron beam receiver;
   article feeding means for feeding said article; and
   a sterilization chamber housing said article feeding means therein;
   wherein said sterilization chamber includes an opening defined therein, and said electron beam sterilizer is selectively operable in a sterilization mode in which said irradiation window of said electron beam irradiation unit is disposed in facing relation to said opening of the sterilization chamber and a maintenance mode in which said electron beam irradiation unit is disconnected from said sterilization chamber and connected to said adjustment irradiation box.

* * * * *